United States Patent [19]
Kitano

[11] Patent Number: 6,025,393
[45] Date of Patent: *Feb. 15, 2000

[54] METHOD FOR TREATMENT OF INFLAMMATORY INTESTINAL DISEASES

[75] Inventor: Atsuo Kitano, Sakai, Japan

[73] Assignee: Santen Pharmaceutical Co., Ltd., Osaka, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/766,645

[22] Filed: Dec. 13, 1996

Related U.S. Application Data

[63] Continuation of application No. 08/533,512, Sep. 25, 1995, abandoned.

[51] Int. Cl.[7] .................................................. A61K 31/195
[52] U.S. Cl. ............................................................ 514/562
[58] Field of Search ............................................. 514/562

[56] References Cited

U.S. PATENT DOCUMENTS

| | | | |
|---|---|---|---|
| 4,241,086 | 12/1980 | Iwao et al. | 514/562 |
| 4,255,446 | 3/1981 | Iwao et al. | 514/562 |
| 4,305,958 | 12/1981 | Fujita et al. | 562/426 |
| 4,482,709 | 11/1984 | Iwao et al. | 536/46 |

OTHER PUBLICATIONS

The Merck Index, 11th ed., published by Merck & Co., Inc (N.J.), p. 221, cit.#1447, 1989.

Pharmacy Power–Pak, Continuing Pharmacy Education Inflammatory Bowel Disease Therapy, published by Marion Merrell Dow, Inc., pp. 14–18, 1993.

*Primary Examiner*—Raymond Henley, III
*Attorney, Agent, or Firm*—Frishauf, Holtz, Goodman, Langer & Chick, P.C.

[57] ABSTRACT

This invention relates to a method for treatment of inflammatory intestinal diseases which comprises administering bucillamine or a salt thereof and pharmaceutical acceptable carriers. Bucillamine exhibits an excellent suppressive effect on disorders of the mucous membrane and exhibits a therapeutic effect on ulcerative colitis. Bucillamine is very useful for treatment of inflammatory intestinal diseases.

18 Claims, No Drawings

METHOD FOR TREATMENT OF INFLAMMATORY INTESTINAL DISEASES

This application is a Continuation of application Ser. No. 08/533,512, filed Sep. 25, 1995, now abandoned.

SUMMARY OF THE INVENTION

This invention relates to a method for treatment of inflammatory intestinal diseases such as ulcerative colitis and Crohn's disease which comprises administering bucillamine or a salt thereof and pharmaceutical acceptable carriers.

BACKGROUND OF THE INVENTION

Inflammatory intestinal diseases such as ulcerative colitis and Crohn's disease are intractable chronic diseases and the pathogenesis of such diseases still remains uncertain. Ulcerative colitis is non-specific diffuse inflammatory disease where the mucous membrane of large intestine, especially of colon is eroded and often results in an erosion or ulceration. Crohn's disease is granulomatous inflammatory disease accompanied by fibrosing or ulceration of any part of gastrointestinal mucous membrane. A medical treatment or surgical treatment can be applied for treatment of intestinal diseases. However, a medical treatment is preferable because recurrence of a disease is often observed after a surgical treatment. A medical treatment is classified as a dietary treatment and a medicinal treatment. A dietary treatment consists of parental nutrition and elemental enteral hyperalimentation. A dietary treatment does not stimulate the intestine and an prevent recurrence of a disease. For a medicinal treatment, steroids, salazosulfapyridine, immunosuppressors, etc. can be used, but known drugs in such field have side effects and the efficacy is not satisfactory. There have been many studies on a drug for treatment of inflammatory intestinal diseases, but a development of new drugs is still desired.

It has been already that bucillamine is a safe and very useful compound applicable for a therapeutic agent for rheumatic disease, cataract, diabetes, osteoporosis or cystinuria, a dissolving agent for sputum or a suppressive agent for liver disorders (Japanese Patent Publication; 11888/1985, 5388/1981, 13922/1987, 13964/1988, and Japanese Unexamined Japanese Patent Publication; 154721/1992, 154722/1922, 342524/1992, 186341/1993).

DETAILED DESCRIPTION OF THE INVENTION

This invention relates to a method for treatment of inflammatory intestinal diseases which comprises administering bucillamine of the formula [I] or a salt thereof and pharmaceutical acceptable carriers.

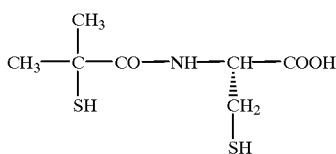

[I]

Inflammatory intestinal diseases mean intractable chronic diseases where the mucous membrane of intestine is damaged by an uncertain cause. Typical examples of such diseases are ulcerative colitis and Crohn's disease. Ulcerative colitis is a non-specific diffuse inflammatory disease where the mucous membrane of the large intestine, especially of colon is eroded and often results in an erosion or ulceration. Crohn's disease is granulomatous inflammatory disease accompanied by fibrosing or ulceration of any part of the gastrointestinal mucous membrane. A medical treatment or surgical treatment can be applied for a treatment of such diseases. However, a medical treatment is preferable because recurrence of a disease is often observed after a surgical treatment. A medical treatment is classified as a dietary treatment and a medicinal treatment. This invention relates to a medicinal treatment of inflammatory intestinal diseases. For a medicinal treatment, steroids, salazosulfapyridine, immunosuppressors, etc. can be used, but known drugs in such field have many side effects and the efficacy is not satisfactory. Thus, the inventor studied to find a useful drug for treatment of inflammatory intestinal diseases and focused on bucillamine. Bucillamine is a known compound having various pharmacological effects and is actually used for the treatment of rheumatoid arthritis. The inventor studied the action of bucillamine precisely. First, the inventor studied the effect of bucillamine on disorders of the mucous membrane of the intestine using experimental colitis and found that bucillamine exhibits an excellent suppressive effect on disorders of the mucous membrane. Second, the inventor studied the clinical effect on ulcerative colitis and found the bucillamine exhibits a therapeutic effect on ulcerative colitis. Details are explained in the following EXAMPLE. The experimental results prove that bucillamine is very useful for treatment of inflammatory intestinal diseases. Bucillamine can be administered orally or parenterally. Examples of dosage forms are tablets, granules, powders, capsules and injections. Examples of the preparations are shown in the article set forth in the following EXAMPLE. But, the preparations disclosed in Japanese Patent Publication 5388/1981 or 11888/1985, etc., or the preparations on the market can be also used clinically. The dosage of bucillamine can be adjusted depending on symptoms, age, dosage form, etc. The usual daily dosage can be 10–1000 mg, in one or a few divided doses.

EXAMPLE

1. Preparation

Examples of formulations are shown below.

| | |
|---|---|
| 1) oral formulation | |
| a) tablet | |
| bucillamine | 100 mg |
| ethyl cellulose | 50 mg |
| crystalline cellulose | 80 mg |
| carboxyl methyl cellulose | 7 mg |
| magnesium stearate | 3 mg |
| total | 240 mg |

The tablet may be treated by film coating and followed by sugar coating.

| | |
|---|---|
| b) granule | |
| bucillamine | 100 mg |
| polyvinyl pyrroridone | 25 mg |
| lactose | 365 mg |
| tarc | 10 mg |
| total | 500 mg |
| c) powder | |
| bucillamine | 100 mg |
| lactose | 500 mg |
| starch | 370 mg |
| colloidal silica | 30 mg |
| total | 1000 mg |

-continued

| | | |
|---|---|---|
| d) capsule | | |
| bucillamine | 100 mg | |
| lactose | 32 mg | |
| crystalline cellulose | 56 mg | |
| colloidal silica | 2 mg | |
| total | 190 mg | |

2) injection

A solution for injection can be prepared by dissolving 250 mg of bucillamine in 5 ml of sterile purified water and adjusting pH to 6.5–7.0.

2. Pharmacological Test 1) non-clinical test

The effect of bucillamine on inflammatory intestinal diseases was examined using carrageenan—induced colitis which resembles human colitis. The experimental results were evaluated according to the scoring method reported in Jap. J. Gastroenterol., 90, 24–32 (1993), etc.

(Experimental Method)

Animals:

Male New Zealand white rabbits weighing about 2.2 kg were used. They were raised on a standard pellet diet in an air-conditioned comfortable room until sacrificed painlessly.

Production of experimental colitis:

Experimental colitis was induced according to the method reported in Cancer Res., 46, 1374–1376 (1986), etc. 2 ml of complete Freund's adjuvant containing 1% λ-degraded carrageenan (1% carrageenan, molecular weight: about 30000) was injected subcutaneously in the vicinity of the trapezius muscle to sensitize the animals. During the 8 week period starting from one week after the injection, free access was allowed to the animals to 400 ml/day of drinking water containing 0.3% carrageenan.

Treatment with bucillamine:

Bucillamine was added to the drinking water, in addition to carrageenan. The amount of bucillamine added was adjusted to a dose of 100 or 300 mg/kg/day when the drinking water was taken completely. Control rabbits were not treated with bucillamine.

Histology:

All rabbits were sacrificed at the end of the treatment period. The colon (20 cm from the anus) was obtained surgically and fixed in 10% formalin. The organ was dehydrated, embedded in paraffin, cut into sections, and stained with hematoxylin and eosin. The inflammatory mucosal changes such as abnormalities of surface epithelium, crypt abscess, inflammatory cell infiltration, atrophy, goblet cell depletion, ulceration, erosions and oedema were evaluated according to the known method reported in Jap. J. Gastroenterol., 90, 24–32 (1993) using point scores shown in Table 1.

TABLE 1

| Mucosal damage scores | | |
|---|---|---|
| Lesional findings | Degrees of injury | Score values |
| Surface epithelium | Extensive defect | 3 |
| | Partial defect | 2 |
| | Deformation | 1 |
| | None | 0 |
| Crypt abscess | Strong | 5 |
| | Weak | 3 |
| | None | 0 |

TABLE 1-continued

| Mucosal damage scores | | |
|---|---|---|
| Lesional findings | Degrees of injury | Score values |
| Inflammatory cell infiltratio (lamina propria) | Abundant | 3 |
| | Moderate | 2 |
| | Slight | 1 |
| | Normal | 0 |
| Atrophic change | Extensive and high occurrence | 3 |
| | Extensive and slight occurrence | 2 |
| | Partial occurrence | 1 |
| | None | 0 |
| Muscularis | Defect | 3 |
| | Swelling | 2 |
| | No change | 0 |
| Goblet cell depletion | + | 2 |
| | − | 0 |
| Ulcer (erosion) | + | 5 |
| | − | 0 |
| Oedema | + | 2 |
| | − | 0 |

(Result)

The results were shown in Table 2 where colonic mucosal damage was represented by the total score (mean value) of each lesional findings.

TABLE 2

| | total score |
|---|---|
| Control group (three rabbits) | 16,00 |
| Group (seven rabbits) given 100 mg/kg/day of bucillamine | 11,20 |
| Group (seven rabbits) given 300 mg/kg/day of bucillamine | 8,86 |

As shown in Table 2 the animals treated with bucillamine had milder damage than the untreated control animals. In addition, the higher dose (300 mg/kg) of bucillamine exerted a stronger preventive effect on colonic mucosal damage.

2) clincal test

A tablet containing 100 mg of bucillamine was administered to two patients with an active ulcerative colitis three times a day for eight weeks. Efficacy was evaluated in clinical symptoms, hematological findings, endoscopic findings and stopathological findings on biopsy specimens. Both cases induced completely remission stage, such as no clinical symptom as diarrhea, bloodstool, and reduced inflammatory index, and no finding ulcer and erosion by endoscopy.

The results of non-clinical and clinical tests shown above prove that bucillamine has excellent effects on mucosal damages and that it is useful for treatment of inflammatory intestine diseases such as ulcerative colitis and Crohn's disease.

What is claimed is:

1. A method for treatment of inflammatory intestinal disease which comprises administering to a patient in need thereof an effective amount of bucillamine or a salt thereof with pharmaceutical acceptable carriers.

2. The method of claim 1, wherein the inflammatory intestinal disease is ulcerative colitis.

3. The method of claim 1, wherein the inflammatory intestinal disease is Crohn's disease.

4. The method of claim 1, wherein the bucillamine is administered in a daily dose of 10 to 1000 mg.

5. The method of claim 1, wherein the bucillamine is administered orally.

6. The method of claim 1, wherein the bucillamine is administered parenterally.

7. The method of claim 2, wherein the bucillamine is administered in a daily dose of 10 to 1000 mg.

8. The method of claim 2, wherein the bucillamine is administered orally.

9. The method of claim 2, wherein the bucillamine is administered parenterally.

10. The method of claim 3, wherein the bucillamine is administered in a daily dose of 10 to 1000 mg.

11. The method of claim 3, wherein the bucillamine is administered orally.

12. The method of claim 3, wherein the bucillamine is administered parenterally.

13. The method of claim 4, wherein the bucillamine is administered orally.

14. The method of claim 4, wherein the bucillamine is administered parenterally.

15. The method of claim 7, wherein the bucillamine is administered orally.

16. The method of claim 7, wherein the bucillamine is administered parenterally.

17. The method of claim 10, wherein the bucillamine is administered orally.

18. The method of claim 10, wherein the bucillamine is administered parenterally.

\* \* \* \* \*